US010624879B2

(12) United States Patent
Nam et al.

(10) Patent No.: US 10,624,879 B2
(45) Date of Patent: *Apr. 21, 2020

(54) LIQUID PHARMACEUTICAL COMPOSITION

(71) Applicant: Ferring International Center S.A., St. Prex (CH)

(72) Inventors: Bong Gil Nam, Seoul (KR); Byeung Jun Lee, Gyeonggi-do (KR); Shunji Jin, Gyeonggi-do (KR)

(73) Assignee: FERRING INTERNATIONAL CENTER S.A., St. Prex (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/822,298

(22) Filed: Nov. 27, 2017

(65) Prior Publication Data

US 2018/0235947 A1  Aug. 23, 2018

Related U.S. Application Data

(63) Continuation of application No. 15/214,768, filed on Jul. 20, 2016, now Pat. No. 9,827,231, which is a continuation of application No. PCT/KR2014/005512, filed on Jun. 23, 2014.

(30) Foreign Application Priority Data

Mar. 19, 2014  (KR) .................. 10-2014-0032242

(51) Int. Cl.
| *A61K 9/00* | (2006.01) |
| *A61K 31/194* | (2006.01) |
| *A61K 47/12* | (2006.01) |
| *A61K 47/02* | (2006.01) |
| *A61K 9/08* | (2006.01) |
| *A61K 33/08* | (2006.01) |
| *A61K 31/445* | (2006.01) |
| *A61K 31/4402* | (2006.01) |

(52) U.S. Cl.
CPC ........ *A61K 31/4402* (2013.01); *A61K 9/0095* (2013.01); *A61K 9/08* (2013.01); *A61K 31/194* (2013.01); *A61K 31/445* (2013.01); *A61K 33/08* (2013.01); *A61K 47/02* (2013.01); *A61K 47/12* (2013.01)

(58) Field of Classification Search
None
See application file for complete search history.

(56) References Cited

U.S. PATENT DOCUMENTS

| 5,215,769 A | 6/1993 | Fox et al. |
| 5,498,425 A | 3/1996 | Wood et al. |
| 8,450,338 B2 | 5/2013 | Xu et al. |
| 8,481,083 B2 | 7/2013 | Xu et al. |
| 9,827,231 B2 | 11/2017 | Nam |
| 2013/0018223 A1 | 1/2013 | Joseph et al. |
| 2013/0149390 A1* | 6/2013 | Gorelick ................ A61K 47/26 424/606 |
| 2015/0072014 A1 | 3/2015 | Essakimuthu et al. |
| 2017/0049758 A1 | 2/2017 | Liang et al. |
| 2018/0015078 A1 | 1/2018 | Liang et al. |

FOREIGN PATENT DOCUMENTS

| EP | 0 401 096 A | 12/1990 |
| IN | 1605/CHE/2006 A | 11/2008 |
| JP | S5697248 | 8/1981 |
| JP | H04-234960 A | 8/1992 |
| JP | 2557111 B | 11/1996 |
| JP | H10-327805 A | 12/1998 |
| JP | H11-299454 A | 11/1999 |
| JP | 2002-010765 A | 1/2002 |
| KR | 10-1155099 | 6/2012 |
| KR | 10-1166099 B1 | 6/2012 |
| KR | 2015 0016666 | 2/2015 |
| RU | 2342928 | 1/2009 |
| RU | 2353412 | 4/2009 |
| RU | 2473332 | 1/2013 |
| RU | 2482850 | 5/2013 |
| WO | WO 2017/031121 | 2/1917 |
| WO | WO-91/19692 | 12/1991 |
| WO | WO-01/66083 A1 | 9/2001 |
| WO | WO 2011/078828 | 6/2011 |
| WO | WO-2011/078828 A1 | 6/2011 |
| WO | WO-2011/142731 A2 | 11/2011 |
| WO | WO 2012/102799 | 8/2012 |
| WO | WO-2014/016671 | 1/2014 |
| WO | WO 2014/032108 | 3/2014 |
| WO | WO 2017/031121 * | 2/2017 |

OTHER PUBLICATIONS

Handbook of Pharmaceutical Excipients Sixth Edition, Edited by RC Rowe, PJ Sheskey and ME Quinn; Pharmaceutical Press (2009) (Year: 2009).*
Ferring Pharmaceuticals Inc. Prepopik® Highlights of Prescribing Information (Jul. 2012) (Year: 2012).*
Drugs.com Prepopik—How does this stuff taste? How much do you have to drink?, https://www.drugs.com/answers/prepopik-bowel-preps-before-unable-finish-simply-58434.html (retrieved Jun. 20, 2017, 3 pp) (Year: 2017).*
Albugeaey et al., Tu1037 How Bad Was That Bowel Prep? Results of a Patient Questionnaire Survey at a University Center, *Gastrointestinal Endoscopy*, 2013, 83(5 Suppl.), p. AB539.
Chakraborty et al., United States Food and Drug Administration, Center for Drug Evaluation and Research, Pharmacology Review(s) for Application No. 21-551, Halflytely, 2012, 24 pp.
Drugs.com, Prepopik—How does this stuff taste? How much do you have to drink?, https://www.drugs.com/answers/prepopik-bowel-preps-before-unable-finish-simply-58434.html, retrieved Jun. 20, 2017, 3 pp.

(Continued)

*Primary Examiner* — Dennis Heyer
(74) *Attorney, Agent, or Firm* — Foley & Lardner LLP

(57) ABSTRACT

The present invention provides a physically and chemically stable pharmaceutical liquid composition including sodium picosulfate, magnesium oxide, citric acid and malic acid and methods of making and using such a composition.

19 Claims, 1 Drawing Sheet

(56) References Cited

OTHER PUBLICATIONS

European Search Report in Application No. 14886464.8, dated Sep. 18, 2017, 7 pp.
Ferring Pharmaceuticals Inc., Prepopik® Highlights of Prescribing Information, Jul. 2012, 13 pp.
International Search Report in International Application No. PCT/KR2014/005512, dated Dec. 17, 2014, 13 pp.
Song et al., Effectiveness of Sodium Picosulfate/Magnesium Citrate (PICO) for Colonoscopy Preparation, Ann Coloproctol 2014, 30(5), 222-227.
"Sodium picosulfate," Wikipedia, obtained online, URL: <https://en.wikipedia.org/wiki/Sodium_picosulfate> (downloaded May 2019).
Third Party Observation dated May 28, 2019 in European Application No. 14886464.8.
"Guidance for Industry: Q1A(R2) Stability Testing of New Drug Substance and Products," FDA (Nov. 2003).
"Sodium Picosulfate, Magnesium Oxide, and Anhydrous Citric Acid (PREPOPIK) for Oral Solution," National Drug Monograph (Jun. 2013) Available online, URL: <https://www.pbm.va.gov/clinicalguidance/drugmonographs/PicosulfateMagnesiumOxideCitricAcidPREPOPIKMonograph.pdf>.
"UKPAR, Sodium Picosulfate 5mg/5ml Oral Solution, PL 17496/0022" Medicines & Healthcare Products Regulatory Agency, (2007).
Barkun et al., "Commonly Used Preparations for Colonoscopy: Efficacy, Tolerability and Safety—A Canadian Association of Gastroenterology Position Paper," Can. J. Gastroenterol., vol. 20, No. 11, pp. 699-710, (Nov. 2006).
Crowley, "Solutions, Emulsions, Suspensions, and Extracts," Remington: The Science and Practice of Pharmacy, 21st Edition, Chapter 39, pp. 745-775.
Du et al., "Comparison of Bowel Preparation Quality With a Bowel Purgative Containing Sodium Picosulfate, Magnesium Oxide and Citric Acid Versus a PEG-ELS Solution: A Prospective RCT in China Using Chinese Language Validated Ottawa Scale," Gastrointestinal Endoscopy, SU1303, vol. 75, No. 4S, p. AB286, (2012).
Ducolax Pico Liquid Package Leaflet (Jun. 2013).
Confidential Detailed Factual and Legal Basis for Paragraph IV Certification That U.S. Pat. No. 9,827,231 is Invalid, Unenforceable, and/or Will Not Be Infringed (Apr. 4, 2019).
PDR, "Physicians' Desk Reference 2013," 67th Edition (2012), (Prepopik Prescribing Information).
Savic et al., "Monitoring of Thermal and Oxidation Stability of Sodium Picosulfate by Modified RP-HPLC Method," Chemical Industry & Chemical Engineering Quarterly 16 (1) pp. 103-110 (2010).
Suprep Prescribing Information (Aug. 2010).
Uselton et al., "Assuring Continuous Compliance with Joint Commission Standards: A Pharmacy Guide," Eighth Edition (2010).
Duarte et al., "Organic Acids Concentration in Citrus Juice from Conventional versus Organic Farming," Acta horticulturae, 2012; 933: 601-606.
Sortwell et al., "Improving the Flavor of Fruit Products with Acidulants," Bartek [online]; 1996; downloaded from <URL http://citeseerx.ist.psu.edu/viewdoc/download?doi=10.1.1.548.4424&repl&type=pdf> dated Jun. 30, 2019; 10 pages (1996).
Office Action dated Jul. 10, 2019 in U.S. Appl. No. 15/238,408.
Office Action dated Nov. 14, 2017 in U.S. Appl. No. 15/238,408.
Office Action dated Jul. 2, 2018 in U.S. Appl. No. 15/238,408.
Anonymous., "CHEBI:114786—sodium disulfite," ChEBI [online]; updated Apr. 12, 2016; downloaded from <URL: https://www.ebi.ac.uk/chebi/searchId.do?chebiId=CHEBI:114786> dated Oct. 25, 2019; 4 pages (2016).
Office Action dated Oct. 30, 2019 in U.S. Appl. No. 15/643,727.
"Malic Acid," Handbook of Pharmaceutical Excipients, Sixth Edition, Edited by RC Rowe, PJ Sheskey and ME Quinn; Pharmaceutical Press, pp. 411-413 (2009).
Office Action dated Jan. 16, 2020 in U.S. Appl. No. 15/238,408.
Rabizadeh et al., "Carboxylic acids: effective inhibitors for calcium sulfate precipitation?" Mineralogical Magazine, vol. 78(6), pp. 1465-1472 (Nov. 2014).

* cited by examiner

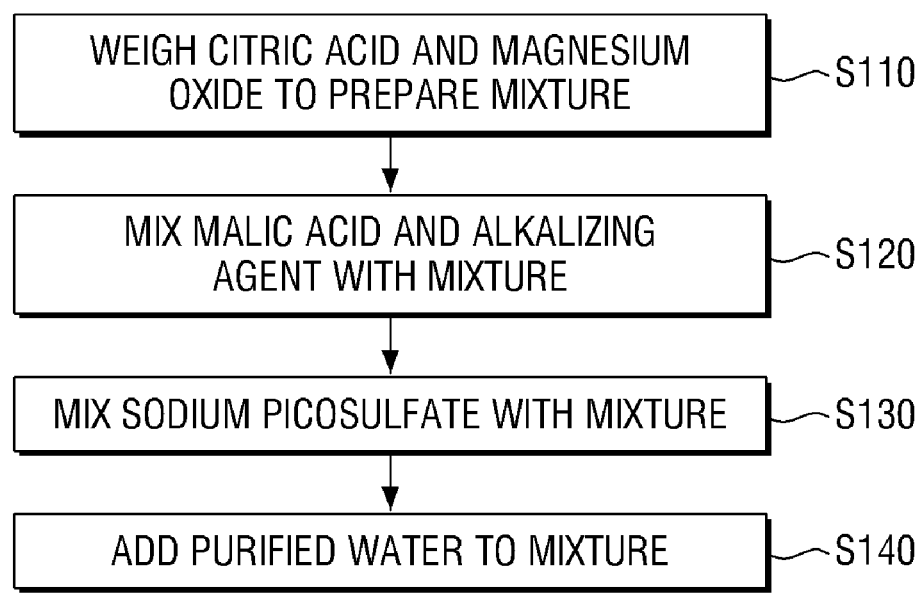

LIQUID PHARMACEUTICAL COMPOSITION

CROSS-REFERENCE TO RELATED APPLICATIONS

This application is a continuation of U.S. application Ser. No. 15/214,768, filed Jul. 20, 2016, which is a continuation of International Appl. No. PCT/KR2014/005512, filed Jun. 23, 2014, which claims the benefit of Republic of Korea Patent Application Number 10-2014-0032242, filed Mar. 19, 2014. The related applications, and PCT International Publication Number WO2015/141897 (the publication of PCT/KR2014/005512), are each hereby incorporated by reference in their entirety.

TECHNICAL FIELD

The present invention relates to a pharmaceutical liquid composition, and more particularly to a physically and chemically stable pharmaceutical liquid composition including sodium picosulfate, magnesium oxide, citric acid and malic acid.

BACKGROUND

A medicine including citric acid magnesium oxide and sodium picosulfate is used as a purgative for pretreatment at the time of surgery, colonoscopy or colon X-ray inspection, and is currently commercially available as the name of Picolight power. This medicine is white powder which is used by being dissolved in water when taken orally.

The medicine in the dosage form of powder should be taken by dissolving one package in a suitable amount of water. However, some patients may feel inconvenient when dissolving the medicine in water, and some patients who fail to recognize how to use properly may drink water after putting the powder into the mouth. In this case, exothermic reaction occurring when the powder is dissolved in water may burn the patient's mouth.

Thus, the medicine in the form of powder may be dissolved in water in advance and stored in a refrigerator or another storage space before being taken. However, in this case, citric acid and magnesium oxide that are chief ingredients may react with each other to become magnesium citrate, and the remaining magnesium oxide after reaction may accelerate the precipitation of the magnesium citrate over time to sink to the bottom. Therefore, if the medicine is not diluted well with water when taken, a proper effect cannot be achieved because the precipitated amount cannot be taken. As the pH of the medicine is kept low, the amount of precipitation tends to be reduced. However, in this case, there arises a problem such that sodium picosulfate becomes unstable.

Therefore, in order to solve the problems described above, there is a demand for a physically and chemically stable pharmaceutical liquid composition.

SUMMARY

In view of the above, the present invention provides a physically and chemically stable pharmaceutical liquid composition including sodium picosulfate, magnesium oxide and citric acid.

However, objects of the present invention are not restricted to the one set forth herein. The above and other objects of the present invention will become more apparent to one of ordinary skill in the art to which the present invention pertains by referencing the detailed description of the present invention given below.

DETAILED DESCRIPTION

In accordance with an aspect of the present invention, there is provided a pharmaceutical liquid composition including sodium picosulfate, magnesium oxide, citric acid and malic acid.

The pharmaceutical liquid composition may be used for colon cleaning as a purgative for pretreatment at the time of surgery, colonoscopy or colon X-ray inspection.

A one-time dose of the liquid composition may be different according to the content of an effective ingredient, but may range from 50 mL to 500 mL as a non-limiting example. In an exemplary embodiment, it may range from 100 mL to 300 mL or may range from 150 mL to 200 mL, but it is not limited thereto.

In order to remove the inconvenience when the medicine in the form of powder is taken by dissolving powder in water, it is intended to change the dosage form from powder to liquid. However, the present invention provides a pharmaceutical liquid composition which is physically and chemically stable when stored.

As one example, in the pharmaceutical liquid composition, for 24 months, a content change of each ingredient may be within ±5.0 wt. % (weight percent) with respect to the weight of each ingredient, and impurities. Substance A related to sodium picosulfate (4-[(pyridine-2-yl)(4-hydroxyphenyl)methyl]phenyl sodium sulfate) may be generated at 2.0 wt. % or less. Further, the precipitate may not occur, or may occur at 5.0 vol. % (volume percent) or less.

According to experiments by the inventors of the present invention, in the case of using organic acid or inorganic acid other than malic acid, it is difficult to expect the stability as described above. The malic acid may include both l-malic acid and d-malic acid.

In order to have the stability described above, in one preferred example, the pH of the pharmaceutical liquid preparation may range from 4.1 to 5.4.

According to experiments by the inventors of the present invention, it has been confirmed that superior stability is exhibited in the pH range. If the pH of the pharmaceutical liquid composition is less than 4.1, Substance A related to sodium picosulfate increases, and it is not preferable because the patient may feel uncomfortable with strong sourness when taking the medicine. On the other hand, if the pH of the pharmaceutical liquid composition is greater than 5.4, it is not preferable because it is difficult to dissolve magnesium oxide which causes the precipitation.

The pharmaceutical liquid composition of the present invention may include a variety of excipients and purified water. The purified water is used in order to prepare the medicine in the form of liquid, and the excipients may be used for the excellent taste to increase the medication compliance and the stability of the pharmaceutical liquid composition.

For example, the excipients may include, but not limited to, a pH adjuster, a stabilizer, a preservative, a sweetener and a fragrance ingredient.

The pH adjuster may be an alkalizing agent. In the case of the alkalizing agent, it is possible to adjust a reduction in pH due to the malic acid.

As the alkalizing agent, for example, sodium hydroxide, potassium hydroxide, sodium bicarbonate, ammonia solution, potassium citrate, triethanolamine and sodium citrate and the like may be used, but it is not limited thereto. In an exemplary embodiment, sodium hydroxide, potassium hydroxide, sodium citrate, and the like may be used, but it is not limited thereto.

The sodium picosulfate, magnesium oxide, citric acid and malic acid may have a weight ratio of 0.003 to 0.009:1 to 3:3.5 to 10.5:0.01 to 13 (sodium picosulfate:magnesium oxide:citric acid:malic acid).

An exemplary method of preparing a pharmaceutical liquid composition of the present invention will be described below.

The method may include the steps of weighing citric acid and magnesium oxide to prepare a mixture, mixing malic acid and a pH adjuster with the prepared mixture, mixing sodium picosulfate with the mixture, and adding purified water to the mixture.

The weighing may also include the step of weighing and separately preparing each of ingredients to be used.

In one example, before adding the purified water, a sweetener, a fragrance ingredient, or a mixture thereof may be added to the mixture or sterilized mixture. The sweetener and/or fragrance ingredient may be used for the excellent taste to increase the medication compliance.

Advantageous Effects

Embodiments of the present invention provide at least the following effects.

By providing a pharmaceutical liquid composition including sodium picosulfate, magnesium oxide, citric acid and malic acid, it is possible to increase the medication compliance and convenience and the ease of storage and transport.

The effects of the present invention are not limited to the above-described effects and other effects which are not described herein will become apparent to those skilled in the art from the following description.

DESCRIPTION OF DRAWINGS

FIG. 1 is a process flow diagram illustrating a method of manufacturing a pharmaceutical liquid composition according to an embodiment of the present invention.

OTHER EMBODIMENTS

Although the present invention may be variously changed and include several embodiments, particular embodiments shown in the drawings will be described in detail in a detailed description. However, it is to be understood that the present invention is not limited to the particular embodiments, and various changes, equivalences and substitutions may be made without departing from the scope and spirit of the invention.

EXAMPLES

Example 1

A pharmaceutical liquid composition was prepared by dissolving, in purified water in a weight ratio of 75, sodium picosulfate:magnesium oxide:citric acid:dl-malic acid in a weight ratio of 0.005:1.75:6:4.19, sodium benzoate in a weight ratio of 0.043 as a preservative, disodium edetate hydrate in a weight ratio of 0.035 as a stabilizer, sodium hydroxide in a weight ratio of 2.1 as a pH adjuster, acesulfame potassium in a weight ratio of 0.1, and sucralose in a weight ratio of 0.1 as a sweetener, and a fragrance ingredient in orange flavor in a weight ratio of 0.043.

Comparative Example 1

A powder composition was prepared by including sodium picosulfate:magnesium oxide:citric acid in a weight ratio of 0.005:1.75:6, sodium hydrogen carbonate in a weight ratio of 0.21 as an excipient, acesulfame potassium qs (quantum satis) as a sweetener, and a fragrance ingredient having orange flavor qs (quantum satis).

Example 2

The contents of sodium picosulfate, magnesium oxide and citric acid that are main components of a solution obtained by dissolving the liquid composition of Example 1 in water of 150 mL were compared with those of a solution obtained by dissolving the powder composition of Comparative Example 1 in water of 150 mL. The content comparison method is an experiment method pursuant to British Pharmacopoeia 2004 Compound Sodium Picosulfate Powder for Oral Solution and the measurement was made by high performance liquid chromatography. The results are shown in Table 1 below.

TABLE 1

| Ingredient Name | Content Criteria | Example 1 | Comparative Example 1 |
| --- | --- | --- | --- |
| Sodium picosulfate | 90.0~110.0% | 100.7% | 100.1% |
| Magnesium oxide | 90.0~110.0% | 101.0% | 101.4% |
| Citric acid | 90.0~110.0% | 100.1% | 99.7% |

As a result of the experiment, it can be seen from Table 1 that there is no substantial difference between the contents of the main components of Example 1 and Comparative Example 1. Therefore, both the powder composition and the liquid composition are considered to have the same effect as a colon cleanser.

Example 3

A liquid composition was prepared by dissolving, in purified water in a weight ratio of 75, sodium picosulfate:magnesium oxide:citric acid in a weight ratio of 0.005:1.75:6, and adding, as a solubilizing agent, each of polyoxyethylene hydrogenated castor oil, polyethylene sorbitan monooleate, polyoxyethylene octyl dodecyl ether, polysorbate 20, polysorbate 60 and polysorbate 80 at 5.0 wt. % with respect to the total liquid weight. The liquid composition was left under the room temperature conditions (25° C., 60%) to check whether precipitation occurs, and a time point (day) when precipitation occurs at 5.0 vol. % on the bottom of a sample container was measured. The results are shown in Table 2 below.

TABLE 2

| Raw Material Name | Room Temperature Conditions (when precipitation occurs: day) |
| --- | --- |
| Polyoxyethylene hydrogenated castor oil | 20 |
| Polyethylene sorbitan monooleate | 17 |
| Polyoxyethylene octyl dodecyl ether | 17 |
| Polysorbate 20 | 23 |

TABLE 2-continued

| Raw Material Name | Room Temperature Conditions (when precipitation occurs: day) |
|---|---|
| Polysorbate 60 | 22 |
| Polysorbate 80 | 20 |

As can be seen in Table 2, it can be confirmed that precipitates are formed at 5.0 vol. % or more as a result of applying a solubilizing agent, and the solubilizing agent does not contribute to prevention of precipitation.

Example 4

A liquid composition was prepared by dissolving, in purified water in a weight ratio of 75, sodium picosulfate:magnesium oxide:citric acid in a weight ratio of 0.005:1.75:6, using, as organic acid in a weight ratio of 4.19, each of citric acid, dl-malic acid, maleic acid, tartrate, fumaric acid, lactic acid, sodium citrate, aspartic acid, succinic acid, glutamic acid, hydrochloric acid, phosphoric acid, sulfuric acid and acetic acid, and adding, as a pH adjuster, sodium hydroxide in a weight ratio of 2.1 for each pH. The liquid composition was left for 24 months under the room temperature conditions (25° C., 60%) to check whether precipitation occurs. A time point (day) when precipitation occurs at 5.0 vol. % on the bottom of a sample container was measured and shown in Table 3 below. The content of the substance related to sodium picosulfate produced after 24 months was measured and shown in Table 4 below.

TABLE 3

| Raw Material Name | pH | Room Temperature Conditions (when precipitation occurs: day) |
|---|---|---|
| Sodium hydroxide + Citric acid | 5.4 | 2 |
| | 4.7 | 18 |
| | 4.1 | 280 |
| Sodium hydroxide + dl-malic acid | 5.4 | — |
| | 4.7 | — |
| | 4.1 | — |
| Sodium hydroxide + Maleic acid | 5.4 | 2 |
| | 4.7 | 10 |
| | 4.1 | 350 |
| Sodium hydroxide + Tartrate | 5.4 | 2 |
| | 4.7 | 2 |
| | 4.1 | 77 |
| Sodium hydroxide + Fumaric acid | 5.4 | 2 |
| | 4.7 | 18 |
| | 4.1 | 98 |
| Sodium hydroxide + Lactic acid | 5.4 | 2 |
| | 4.7 | 14 |
| | 4.1 | 105 |
| Sodium hydroxide + Sodium citrate | 5.4 | 2 |
| | 4.7 | 10 |
| | 4.1 | 91 |
| Sodium hydroxide + Aspartic acid | 5.4 | 2 |
| | 4.7 | 18 |
| | 4.1 | 77 |
| Sodium hydroxide + Succinic acid | 5.4 | 2 |
| | 4.7 | 18 |
| | 4.1 | 98 |
| Sodium hydroxide + Glutamic acid | 5.4 | 2 |
| | 4.7 | 14 |
| | 4.1 | 98 |

As can be seen in Table 3, it can be confirmed that precipitation occurs within 24 months in all cases of organic acids other than malic acid.

TABLE 4

| Raw Material Name | pH | Room Temperature Conditions (wt. %) |
|---|---|---|
| Sodium hydroxide + Citric acid | 5.4 | 0.19 |
| | 4.7 | 0.32 |
| | 4.1 | 2.61 |
| Sodium hydroxide + dl-malic acid | 5.4 | 0.25 |
| | 4.7 | 0.39 |
| | 4.1 | 1.98 |
| Sodium hydroxide + Maleic acid | 5.4 | 0.31 |
| | 4.7 | 0.49 |
| | 4.1 | 2.91 |
| Sodium hydroxide + Tartrate | 5.4 | 0.26 |
| | 4.7 | 0.46 |
| | 4.1 | 2.97 |
| Sodium hydroxide + Fumaric acid | 5.4 | 0.18 |
| | 4.7 | 0.60 |
| | 4.1 | 2.75 |
| Sodium hydroxide + Lactic acid | 5.4 | 0.26 |
| | 4.7 | 0.74 |
| | 4.1 | 2.74 |
| Sodium hydroxide + Sodium citrate | 5.4 | 0.18 |
| | 4.7 | 0.46 |
| | 4.1 | 2.25 |
| Sodium hydroxide + Aspartic acid | 5.4 | 0.21 |
| | 4.7 | 0.58 |
| | 4.1 | 2.95 |
| Sodium hydroxide + Succinic acid | 5.4 | 0.24 |
| | 4.7 | 0.66 |
| | 4.1 | 2.18 |
| Sodium hydroxide + Glutamic acid | 5.4 | 0.15 |
| | 4.7 | 0.49 |
| | 4.1 | 2.27 |

As can be seen in Table 4, it was confirmed that in the case of including malic acid, Substance A related to sodium picosulfate (4-[(pyridine-2-yl)(4-hydroxyphenyl)methyl]phenyl sodium sulfate) is generated at 2.0 wt. % or less in the above-mentioned pH range.

Hereinafter, embodiments of the present invention will be described with reference to the accompanying drawings.

FIG. 1 is a process flow diagram illustrating a method of preparing a pharmaceutical liquid composition according to an embodiment of the present invention.

The method of preparing a pharmaceutical liquid composition may include the steps of weighing citric acid and magnesium oxide to prepare a mixture (S110), mixing malic acid and sodium hydroxide with the mixture prepared in step S110 (S120), mixing sodium picosulfate with the mixture prepared in step S120 (S130), and adding purified water to the mixture in step S130 (S140).

In step S110, a pH adjuster, a stabilizer, a sweetener and the like may be added to the mixture.

In some cases, step S110 and step S120 may be performed at the same time, and steps S110, S120 and S130 may be performed at the same time. Further, although steps S110, S120 and S130 have been illustrated in the order mentioned, the order is not limited thereto.

Although the embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A pharmaceutical composition comprising sodium picosulfate, magnesium oxide, citric acid, and malic acid, wherein the pharmaceutical composition is a solution with a pH in the range from 4.1 to 5.4.

2. The pharmaceutical composition of claim 1, wherein the sodium picosulfate, the magnesium oxide, the citric acid, and the malic acid are present in a weight ratio of 0.003 to 0.009:1 to 3:3.5 to 10.5:0.01 to 13 (sodium picosulfate: magnesium oxide:citric acid:malic acid).

3. The pharmaceutical composition of claim 1, wherein Substance A related to sodium picosulfate is generated in an amount of about 2.0 wt. % or less when the composition is left at room temperature for 24 months.

4. The pharmaceutical composition of claim 1, wherein precipitation occurs at about 5.0 vol. % or less when the composition is left at room temperature for 24 months.

5. The pharmaceutical composition of claim 1, wherein the composition further comprises one or more excipients chosen from pH adjusters, stabilizers, preservatives, sweeteners, and fragrance ingredients.

6. The pharmaceutical composition of claim 1, wherein the composition further comprises acesulfame potassium.

7. The pharmaceutical composition of claim 1, wherein the composition further comprises disodium edetate.

8. The pharmaceutical composition of claim 1, wherein the composition further comprises sodium benzoate.

9. The pharmaceutical composition of claim 1, wherein the composition further comprises sodium hydroxide.

10. The pharmaceutical composition of claim 1, wherein the composition further comprises sucralose.

11. A pharmaceutical composition comprising sodium picosulfate, magnesium oxide, citric acid, and malic acid, wherein the pharmaceutical composition is a liquid with a pH ranging from 4.1 to 5.4, and further wherein the sodium picosulfate, the magnesium oxide, the citric acid, and the malic acid are present in a weight ratio of about 0.005:1.75: 6:4.19 (sodium picosulfate:magnesium oxide:citric acid: malic acid).

12. The pharmaceutical composition of claim 11, wherein Substance A related to sodium picosulfate is generated in an amount of about 2.0 wt. % or less when the composition is left at room temperature for 24 months.

13. The pharmaceutical composition of claim 11, wherein when the composition is left at room temperature for 24 months, precipitation occurs at about 5.0 vol. % or less.

14. The pharmaceutical composition of claim 11, wherein the composition further comprises one or more excipients chosen from pH adjusters, stabilizers, preservatives, sweeteners, and fragrance ingredients.

15. The pharmaceutical composition of claim 11, wherein the composition further comprises acesulfame potassium.

16. The pharmaceutical composition of claim 11, wherein the composition further comprises disodium edetate.

17. The pharmaceutical composition of claim 11, wherein the composition further comprises sodium benzoate.

18. The pharmaceutical composition of claim 11, wherein the composition further comprises sodium hydroxide.

19. The pharmaceutical composition of claim 11, wherein the composition further comprises sucralose.

* * * * *